US 9,248,036 B2

(12) United States Patent
Dorn et al.

(10) Patent No.: US 9,248,036 B2
(45) Date of Patent: *Feb. 2, 2016

(54) METHOD OF TRANSFERRING A STENT DEVICE FROM A CRIMPING HEAD TO AN OUTER SHEATH OF A STENT DEVICE DELIVERY SYSTEM

(71) Applicant: C. R. Bard, Inc., Murray Hill, NJ (US)

(72) Inventors: Jurgen Dorn, Neulussheim (DE); Beate Walter, Stutensee (DE)

(73) Assignee: C. R. BARD, INC., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/796,801

(22) Filed: Jul. 10, 2015

(65) Prior Publication Data
US 2015/0313733 A1 Nov. 5, 2015

Related U.S. Application Data

(63) Continuation of application No. 13/120,604, filed as application No. PCT/EP2009/063053 on Oct. 7, 2009, now Pat. No. 9,089,449.

(30) Foreign Application Priority Data

Oct. 8, 2008 (GB) .................................. 0818450.9

(51) Int. Cl.
*A61F 2/95* (2013.01)
*A61F 2/82* (2013.01)

(52) U.S. Cl.
CPC ........... *A61F 2/82* (2013.01); *A61F 2230/0069* (2013.01); *A61F 2240/002* (2013.01)

(58) Field of Classification Search
CPC ............... A61F 2/82; A61F 2240/002; A61F 2230/0069; A61F 2/966; A61F 2250/0025; A61F 2002/9522; Y10T 29/49895; Y10T 29/49936; Y10T 29/49938; Y10T 29/4994
USPC ............... 29/507, 508, 521, 522.1, 523, 90.7; 72/402, 370.04, 370.12, 370.21; 623/1.11, 1.12
See application file for complete search history.

(56) References Cited

U.S. PATENT DOCUMENTS 5,702,418 A * 12/1997 Ravenscroft ............... A61F 2/95
606/108
5,992,000 A 11/1999 Humphrey et al.
(Continued)

FOREIGN PATENT DOCUMENTS

WO 0062711 A1 10/2000
WO 03034946 A1 5/2003
(Continued)

OTHER PUBLICATIONS

PCT/EP2009/063053 filed Oct. 7, 2009 International Preliminary Report on Patentability dated Sep. 13, 2010.
(Continued)

*Primary Examiner* — David Bryant
*Assistant Examiner* — Steven A Maynard
(74) *Attorney, Agent, or Firm* — Buchalter Nemer, A PLC

(57) ABSTRACT

A method of moving a stent device into an outer sheath of a stent device delivery system is disclosed. The stent device (4) is crimped into a collapsed configuration onto the loading mandrel (6). The loading mandrel is pushed toward the outer sheath as the engaging surfaces (10) resist relative longitudinal movement between the stent device and the loading mandrel to move the stent device into the outer sheath (16). Upon entering the outer sheath, the stent device expands radially until radially constrained by the outer sheath.

19 Claims, 2 Drawing Sheets

(56) References Cited

U.S. PATENT DOCUMENTS

| | | |
|---|---|---|
| 6,168,921 B1 | 1/2001 | Riss et al. |
| 6,186,921 B1 | 2/2001 | Kotera |
| 6,360,577 B2 | 3/2002 | Austin |
| 6,387,117 B1 | 5/2002 | Arnold, Jr. et al. |
| 6,451,047 B2 * | 9/2002 | McCrea ............ A61F 2/06 623/1.13 |
| 7,316,147 B2 | 1/2008 | Perreault et al. |
| 7,867,267 B2 * | 1/2011 | Sullivan ............ A61F 2/95 606/108 |
| 8,287,582 B2 * | 10/2012 | Dorn ............ A61F 2/95 623/1.11 |
| 2002/0099435 A1 * | 7/2002 | Stinson ............ A61F 2/90 623/1.12 |
| 2004/0106977 A1 * | 6/2004 | Sullivan ............ A61F 2/95 623/1.12 |
| 2006/0065193 A1 * | 3/2006 | Pacetti ............ A61F 2/91 118/500 |
| 2006/0142838 A1 | 6/2006 | Molaei et al. |
| 2007/0083256 A1 * | 4/2007 | Dorn ............ A61F 2/95 623/1.12 |
| 2009/0171434 A1 * | 7/2009 | Rusk ............ A61F 2/95 623/1.12 |
| 2011/0167764 A1 | 7/2011 | Dorn |

FOREIGN PATENT DOCUMENTS

| | | |
|---|---|---|
| WO | 2004096091 A8 | 3/2005 |
| WO | 2005070335 A1 | 8/2005 |
| WO | 2010040784 A1 | 4/2010 |

OTHER PUBLICATIONS

PCT/EP2009/063053 filed Oct. 7, 2009 International Search Report dated Nov. 20, 2009.

PCT/EP2009/063053 filed Oct. 7, 2009 Written Opinion dated Nov. 20, 2009.

U.S. Appl. No. 13/120,604, filed Mar. 23, 2011 Non-Final Office Action dated Sep. 5, 2013.

U.S. Appl. No. 13/120,604, filed Mar. 23, 2011 Notice of Allowance dated Mar. 10, 2015.

* cited by examiner

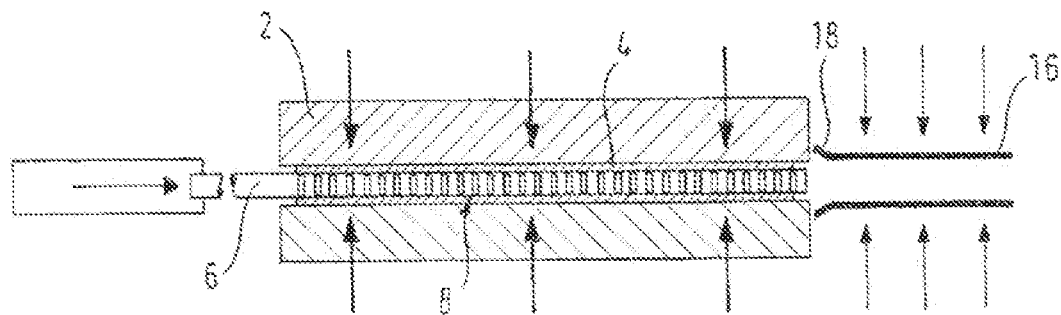
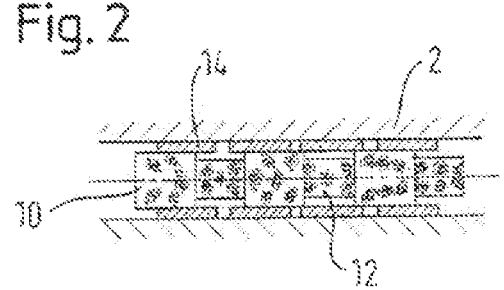
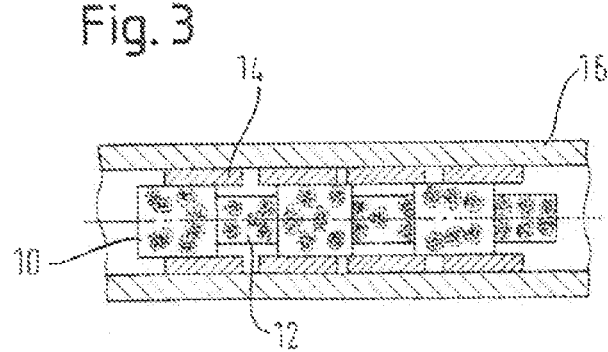

METHOD OF TRANSFERRING A STENT DEVICE FROM A CRIMPING HEAD TO AN OUTER SHEATH OF A STENT DEVICE DELIVERY SYSTEM

PRIORITY

This application is a continuation of U.S. patent application Ser. No. 13/120,604, now U.S. Pat. No. 9,089,449, filed Mar. 23, 2011, as a U.S. national stage application under 35 USC §371 of International Application No. PCT/EP2009/063053, filed Oct. 7, 2009, claiming priority to United Kingdom Patent Application No. 0818450.9, filed Oct. 8, 2008, each of which is incorporated by reference in its entirety into this application.

FIELD OF THE INVENTION

The present invention is concerned with loading of a stent device into an outer sheath of a stent device delivery system. The stent device is subject to radially compressive forces in a crimping head to crimp the stent device into a radially collapsed configuration. The crimped stent device is transferred into the outer sheath of the stent device delivery system by pushing on a loading mandrel.

BACKGROUND OF THE INVENTION

A stent device is a tubular vascular implant that has structure able to support a segment of a blood vessel or other anatomical lumen against collapse, while allowing blood or other bodily fluid to flow through the lumen of the stent device. The stent device is collapsed radially for delivery so that the low profile aids access to the target site. The stent device is delivered with a delivery system to the site where a diseased segment of blood vessel is located and deployed there to support the blood vessel against radial collapse. The stent device is advanced to the site in the collapsed configuration and expanded to contact the inner wall of the blood vessel upon deployment. The delivery system generally comprises an inner catheter to which the stent device is mounted and an outer sheath for constraining the stent device in the collapsed configuration.

There are stent devices that require forced expansion such as by inflating a balloon inside the lumen of the stent device and self-expanding stent devices that are so made that they automatically expand to the radially expanded configuration once given the radial freedom to do so; that is once the stent device is unconstrained by the outer sheath of the delivery system. It is with this latter type of stent device that the present disclosure is primarily concerned.

A stent device includes a tubular framework that is resistant to radial compression so that the blood vessel is maintained open. The stent device may include a cover on the inner and/or the outer surface of the framework, in which case the stent device is often termed a stent graft. If the framework is without inner and outer coverings, the stent device may be labelled a bare stent. Primarily, although not exclusively, the present disclosure is to do with bare stents.

One suitable material for making the framework of the stent device is the nickel titanium shape memory alloy known as NITINOL. Such stents may be put into a collapsed configuration at a low temperature and a memory of a radially expanded configuration is maintained. The nickel titanium material is biologically compatible. The NITINOL stent device returns to the expanded configuration between room temperature and body temperature.

A self-expanding stent device is subjected to axial forces during loading of the stent device into an outer sheath of a delivery system and also during deployment of the stent device from the outer sheath of the delivery system to a site of a vascular lumen where it is to be implanted. During these procedures, the stent device is held axially in position by a delivery pusher or a loading mandrel and the outer sheath is moved axially relative to the stent device and the delivery pusher or the loading mandrel. The delivery pusher and the loading mandrel may be the same element and used both for the loading procedure as well as the deployment procedure. It is with the loading procedure that the present disclosure is concerned, and so we will refer to a loading mandrel, although such a device can in some applications also be used as a delivery pusher.

During the loading procedure, the stent device is crimped by a crimping head into a collapsed configuration and moved into the outer sheath of the delivery system. To move the stent device longitudinally from the crimping head to the outer sheath, frictional forces occur between an inner surface of the crimping head and the outer surface of the stent device. Further, as the transfer proceeds, the outer surface of the stent device will frictionally drag against an inner surface of the outer sheath as it is advanced therewithin.

Therefore, as stent device slides through the crimping head and the outer sheath, drag forces on the stent device from the inner surfaces of the crimping head and the outer sheath translate to axial forces on the stent device. These forces can risk axial damage or buckling of the stent device, as is discussed further below.

U.S. Pat. No. 7,316,147 discloses the use of a pushing mandrel to move the stent from the crimping head into the outer sheath of the delivery system once the diameter size of the stent device has been reduced and crimping is thus complete. The pushing mandrel engages against a proximal end of the stent device. For short, axially strong stents, this design is fine. A particular application may require longer stent devices that are desirably flexible so that the tortuous passageways of the vascular system can be traversed. Flexibility and axial strength present a trade-off in properties, where a more flexible stent device is an axially less strong one. In loading device designs, such as the ones disclosed in U.S. Pat. No. 7,316,147, where a mandrel pushes against a proximal end of a stent device, there is a greater risk with more flexible stent devices of deformation in the longitudinal direction as friction from the inner surfaces of the crimping head and the outer sheath on the stent device induces axial forces that are focused at the proximal end of the stent.

International patent publication number WO 2005/070335 recognised that a problem exists whereby buckling of the start device is caused because the longitudinal force exerted on the stent device by the pushing mandrel to expel it from the crimping head is greater than the column strength of the stent device. The document discloses to use fluid as a boundary layer between blades of the crimping head and the stent device as a friction reducing agent, thereby reducing the longitudinal stress placed on the stent device during transfer from a crimping head to an outer sheath of a stent device delivery system.

International patent publication number WO 2004/096091 proposes to reduce the risk of longitudinal buckling of a stent device during loading by distributing longitudinally the engagement between the stent device and the loading mandrel. This is achieved by the provision of a loading mandrel with protrusions and recesses along an outer surface, where the protrusions are embedded within an inner cover layer, made of expanded polytetrafluouroethylene (ePTFE), of the stent device. The embedded protrusions provide a "form fit" between the stent device and the start device pusher, which means that as the crimping head or outer sheath is moved relative to the stent device, resultant axial forces on the stent device are effectively distributed along it. This publication teaches the use of the inner cover of a stent device to distribute axial loading forces. Bare stents, however, also have application in supporting vascular lumens and a method of effectively distributing loading forces for such stent devices is desirable.

As stent devices grow in length, the frictional forces from the crimping head on the stent device also increases, thereby requiring the start device to be strongly secured on the loading mandrel. Furthermore, and particularly with more flexible stent devices, the risk of buckling of the stent device during loading is desirably reduced by uniformly distributing axial forces along the stent device.

It is, therefore, an object of the present invention to provide a method of loading a stent device, particularly a bare stent, into a stent device delivery system, whereby axial forces on the stent device during transference of the stent device from the crimping head to the outer sheath of the delivery system are effectively distributed uniformly along the stent device.

SUMMARY OF THE INVENTION

The present invention provides a method of moving a stent device into an outer sheath of a stent device delivery system, the method comprising:
  providing a stent device defining a longitudinal axis and having a lumen extending longitudinally therethough;
  providing a loading mandrel;
  crimping the stent device into a collapsed configuration onto the loading mandrel with a force to resiliently deform at least one of an inner surface of the stent device and an outer surface of the loading mandrel in a radial direction to provide engaging surfaces resisting longitudinal movement of the stent device relative to the loading mandrel, said engaging surfaces longitudinally distributed along the inner surface of the stent device;
  pushing the mandrel toward the outer sheath as the engaging surfaces resist relative longitudinal movement between the stent device and the loading mandrel to move the stent device into the outer sheath,
  wherein, upon entering the outer sheath, the stent device expands radially until radially constrained by the outer sheath and the resiliently deformed surface resiliently reforms while maintaining contact between the outer surface of the loading mandrel and the inner surface of the stent device as the loading mandrel moves the stent device longitudinally into the outer sheath.

Such a loading method allows engaging surfaces to be farmed that are distributed along the inner surface of the stent device by making use of the crimping force of the crimping head. An outer sheath ought to be flexible if the tortuous passageways. of the vascular system are to be successfully traversed. Such an cuter sheath may not, therefore, be sufficiently strong to continue to hold the at least one surface deformed. Therefore, upon entering the outer sheath, the stent device expands to relieve the resilient deformation. Nonetheless, even in the reformed state, contact between the loading mandrel and the stent device is maintained, thereby ensuring that the loading mandrel distributes the longitudinal pushing forces to the stent even when it is inside the outer sheath through contact between them.

Preferably, the loading mandrel comprises projections with recesses there between, the projections defining the outer surface of the loading mandrel and the inner surface of the stent device resiliently deforming so that portions thereof are located longitudinally between said recesses to provide said engaging surfaces distributed along the inner surface of the stent device and resisting relative longitudinal movement between the stent device and the loading mandrel.

In this preferred embodiment, the loading mandrel is configured with projections that define spaces for receiving radially inwardly protruding portions of the stent device. The crimping is of such a force as to allow the inner surface of the stent device to extend into the recesses, thereby providing a form fit between the loading mandrel and the stent device for effecting distribution of the force pushing the mandrel longitudinally. The projection and recesses provide a kind of mold against which the stent device is to deform. Once the level of crimping force necessary to deform the stent device is removed and the stent device is within the outer sheath, the stent device expands and moves out of being in the recesses longitudinally between the projections.

Preferably, the stent device comprises a tubular frame for radially supporting a wall of a bodily lumen, wherein the inner surface of the tubular frame is bare to define the inner surface of the stent device.

The tubular frame may be made of a hard material and still be form fitted with the loading mandrel by making use of the crimping force to deform such a material. Thus, the present method of loading a stent device into an outer sheath can distribute loading forces using a form fit method, but can still function with bare stents.

Preferably, the tubular frame is made of metal, preferably a shape memory metal and even more preferably NITINOL.

Preferably, the start device is a self-expandable stent device.

The outer surface of the loading mandrel has a greater hardness than the inner surface of the start device. This allows the stent device to deform against the loading mandrel under the crimping force.

Preferably, the outer surface of the loading mandrel has been treated to have a roughness distributed along the stent device to enhance the friction of said contact with the inner surface of the stent device when the start device is within said outer sheath of the delivery system. In one preferred embodiment, the treatment is to blast the outer surface of the loading mandrel with air carrying a stream of particles to dent the outer surface. Preferably, the blasting treatment is sand blasting.

The enhanced friction between the outer surface of the loading mandrel and the inner surface of the start device permits translation of the longitudinal pushing force on the mandrel to the stent device, even within the outer sheath where the form fit between stent device and the loading mandrel has been relieved by the reduced crimping force therein. Thus, the present invention provides the possibility of simultaneous high friction lock and form fit between the stent device and the loading mandrel. During transfer of the stent device from the crimping head to the outer sheath, there will be stages of advancement, between the stent device being located entirely within the crimping head and the stent device being loaded entirely within the outer sheath, that a portion of the stent device is crimped by the crimping head and a portion of the stent device being constrained by the outer sheath. The former portion will have a form fit between the stent device and the loading mandrel due to the high radial pressure in the crimping head. The latter portion will be absent the form fit due to the lower pressure in the outer sheath, but will make use of high frictional contact between the loading mandrel and the stent device.

The following gives a specific embodiment of the above generally described method of loading a stent into an outer sheath of a delivery system.

BRIEF DESCRIPTION OF THE FIGURES

FIG. 1 shows a crimping head, a stent device on a loading mandrel within the crimping head and an outer sheath of a delivery system arranged to receive the stent device as it leaves the crimping head.

FIG. 2 shows a close up view of the circled part of the stent device, loading mandrel and inner surface of the crimping head of FIG. 1.

FIG. 3 shows a close up view of the stent device and loading mandrel when constrained within the outer sheath.

DETAILED DESCRIPTION OF A PREFERRED EMBODIMENT

Figure 4:
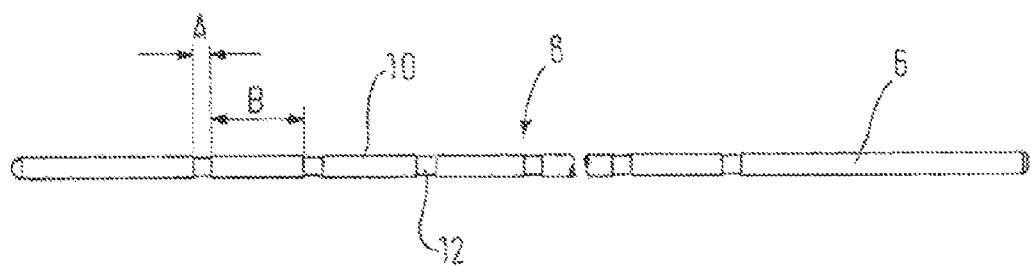
FIG. 4 shows a preferred embodiment for the loading mandrel.

Referring to FIG. 1, a crimping head 2 is shown. The crimping head 2 has a lumen therethrough for receiving a stent device 4 mounted on a loading mandrel 6. The lumen of the crimping head 2 is radially contractible to crimp the stent device 4 into a collapsed configuration. Any stent device crimper known in the art can be used for crimping the stent device. Suitable crimpers are disclosed in U.S. Pat. Nos. 6,360,577, 6,168,921, 6,168,921, 6,387,117 and U.S. Pat. No. 5,992,000. U.S. Pat. No. 6,360,577 discloses an iris-type crimper, where the crimping head is provided by three or more crimping blades operable to force the stent device into a collapsed configuration in an iris-like action. The iris-type crimping head is the preferred one for the crimping head 2 shown in FIG. 1.

The stent device 4 is a self-expandable one having a tubular frame of many stenting turns 14 (the stenting turns are indicated in FIGS. 2 and 3) extending circumferentially around a central longitudinal axis. The stenting turns are made up of zig-zag struts. The zig-zag struts may take a closed zig-zag path about the longitudinal axis to provide a stenting turn in the form of a ring. in an alternative, the zig-zag struts may take a helical path from end of the stent device 4 to the other. In the helical path alternative, the stenting turns are defined by adjacent parts of the helix that travel 360 degrees around the longitudinal axis. The stenting turns are connected to one another by connector struts. The stent device 4 has a lumen extending longitudinally through it. The stent device 4 is a bare stent and thus is absent of an inner or outer cover layer such as inner and outer ePTFE layers. The tubular frame of the stent device 4 is made of NITINOL. Other suitable self-expandable stent device materials known in the art could be used. The stent devices to which the present invention are applicable can be relatively long ones, greater than 80 mm and up to 200 mm, or possibly longer. The stent device 4 shown in FIG. 1 is around 200 mm in length.

Figure 5:
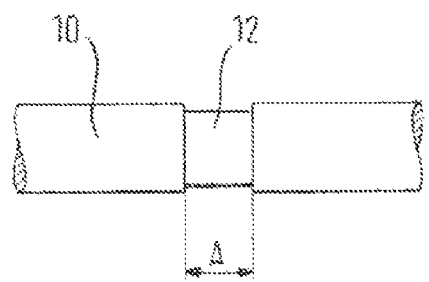
FIG. 5 shows a close up view of the loading mandrel of FIG. 4.

A loading mandrel 6 is also provided and the stent device 4 is mounted to a distal loading portion 8 of the loading mandrel 6, as seen in FIG. 1. The loading mandrel 6 is made of a harder material than the stent device 4, which in this embodiment has been selected as stainless steel. As shown in FIGS. 4 and 5, the loading portion 8 has an outer surface defined by longitudinally spaced protrusions 10 with a recess 12 between each protrusion 10. The loading portion 8 of the loading mandrel 6 is provided as cylindrical segments for the protrusions 10 separated by smaller diameter rings 12 for the recesses 12, where the cylindrical segments and the rings are centred about a central longitudinal axis of the loading mandrel 6. There are approximately two protrusions 10 and two recesses 12 for each stenting turn 14 of the stent device 4. As can be seen from FIGS. 4 and 5, the protrusions 10 are longer than the recesses 12. In the illustrated embodiment, the protrusions 10 are about five times longer than the recesses 12. The outer surface of the loading portion 8 of the loading mandrel 6 is sand blasted, which is indicated by the clouded shading in FIGS. 2 and 3. The protrusions may have a diameter of from five percent to twenty per cent greater than the diameter of the recesses.

FIGS. 4 and 5 are to scale and provide a specific example of the arrangement and dimensions of the loading mandrel 6.

The loading portion 8 includes thirty four recesses of length A of 1 millimetre and thirty three protrusions of length B of 5 millimetres. The diameter of the loading mandrel 6 at the protrusions 10 is 1.2 millimetres, while the diameter of the loading mandrel 6 at the recesses 12 is 1.1 millimetres.

An outer sheath 16 of a delivery system, as shown in FIG. 1, is arranged to receive the stent device 4 from the crimp head 2. At the end of the outer sheath 16 adjacent the crimp head 2, a funnel 18 is attached that tapers inwardly towards the outer sheath 16. The inside-diameter of the outer sheath 16 is marginally greater than the exit diameter of the crimp head 2 so that the stent device is under a greater crimp force in the crimp head 2 than in the outer sheath 16.

A preferred method of crimping the stent device 4 into a collapsed configuration and loading the collapsed stent device 4 into the outer sheath 16 will be described with reference to FIGS. 1, 2 and 3.

The stent device 4 is compressed by crimping blades of the crimping head 2 into a collapsed configuration having a collapsed diameter. The stent device 4 is crimped by the crimping head 2 onto the loading portion 8 of the loading mandrel 6. The NITINOL inner surface of the stent device 4 is resiliently deformed against the stainless steel protrusions 10 of the loading mandrel 6 under the crimping force applied by the crimping head 2. The protrusions 10 cause micro-indentations on the inner surface of the stent device 4, while the portions of the inner surface of the stent device 4 between the protrusions 10 are able to extend so as to be located longitudinally within the recesses 12. Thus, edges of the protrusions 10 and edges of the inner surface of the stent device 4 in the recesses 12 provide engaging surfaces that resist longitudinal movement of the stent device 4 relative to the loading mandrel 6. This is a kind of form fitting engagement between the loading mandrel 6 and the stent device 4, since the protrusions 10 indent into the inner surface of the stent device 4, while the stent device extends into the recesses 12 longitudinally between the protrusions 10.

To transfer the stent device 4 into the outer sheath 16 of the delivery system, an axial force is exerted on the loading mandrel 6. The form fit between the stent device 4 and the loading mandrel 6 means that the axial force on the loading mandrel is translated to an axial force on the stent device 4. The force pushing the loading mandrel is sufficiently strong to overcome the frictional engagement between the stent device 4 and the inner wall defining the lumen of the crimping head 2. Thus, the stent device 4 slides against the inner wall of the crimping head 2 as it moves toward the outer sheath 16 of the delivery system. The protrusions 10 and recesses 12 not only ensure that the stent device 4 is held stationary relative to the loading mandrel 6 as the stent device moves within the crimping head 2, but, by their longitudinal distribution, ensures adequate support along the full extent of the stent device 4 so as to resist buckling of the stent device 4.

The stent device 4 and the loading mandrel 6 are advanced out of the crimping head 2 and the stent device 4 is guided by the funnel 18 into the outer sheath 16. The outer sheath 16 is sized marginally larger than the inner wall of the crimping head 2 so as to allow relief of the micro-indentations in the inner surface of the stent device 4. Portions of the stent device 4 that were resiliently deformed against the protrusions 10 of the loading mandrel 6 will thus resiliently reform as they enter the outer sheath 16 since the crimping force is not as great as in the crimping head 2. The stent device 4 is thus allowed to marginally expand by the degree of indentation in the inner surface of the stent device 4 upon entry into the outer sheath 16 because of the reduced crimping force as a result of the marginally greater diameter of the outer sheath 16 as compared to the diameter of the inner wall of the crimping head 2.

Contact between the protrusions 10 and the inner surface of the stent device 4, however, remains inside the outer sheath 16. This contact is a high friction one, between a sand blasted outer surface of the protrusions 10 of the loading mandrel 6 and an inner surface of the stent device 4. Accordingly, as the stent device 4 begins to enter the outer sheath 16, the form fit relationship between the portion of the loading mandrel 6 inside the outer sheath and the stent device 4 is lost, but a high friction interaction remains. The outer sheath 16 is sized so as to maintain the stent device 4 and the loading mandrel 6 in tight, high friction contact with one another. Thus, as the stent device 4 is advanced, a portion of the stent device 4 inside the crimping head 2 is subject to a form fit relationship with the loading mandrel and a portion of the stent device 4 inside the outer sheath 16. is subject to a friction lock relationship with the outer sheath 16. Accordingly, the stent device 4 is supported by the loading mandrel 6 in a manner distributed along its whole length, including portions in the crimping head 2 and the outer sheath 16, as the stent device is subjected to drag forces from frictional engagement with the crimping head 2 and the outer sheath 16.

The stent device 4 will eventually be advanced by the loading mandrel 6 so that it is positioned entirely within the outer sheath 16. Again, the frictional engagement between the protrusions 10 and the loading mandrel 6 serve to provide longitudinal support to the stent device as the stent device is moved along the outer sheath 16 and in a manner uniformly distributed along the whole length of the stent device 4.

The loading mandrel 6 is made of a hard material in order that the tubular frame of the stout device 4 can be deformed against it. Such a material is inflexible and thus may not be suited for use as a deployment catheter. Accordingly, the loading mandrel 6 is removed from within the stent device 4 so that a delivery catheter can be mounted therein. This may be done by heating the stent device 4, which has up until yet been crimped and transferred to the outer sheath at a temperature below NITIONOL's transition temperature. The stent device 4 may be actively or passively heated above the transition temperature so that the NITINOL strain to return back to its expanded memory condition. This expansion of the stent device 4 is constrained by the outer sheath 16, but may be enough to disengage the inner surface of the stent device 4 from the outer surface of the loading portion 8 of the loading mandrel 6. In this way, the loading mandrel can be retracted from within the stent device 4 and from within the outer sheath 16.

A delivery inner catheter is mounted to the stent device 4 for holding the stent device 4 during retraction of the outer sheath 16 for deploying the stent device 4 at a target stenting treatment site. The delivery inner catheter is preferably of the kind that extends through the lumen of the stent device 4 and forms a support engagement between the inner surface of the stent device and the outer surface of the delivery inner catheter. The engagement between the delivery inner catheter and the stent device 4 serves to support the stent device along its length and resist relative movement therebetween during deployment as the outer sheath 16 drags over the outer surface of the stent device 4. The delivery inner catheter can be mounted within, and then engaged with, the stent device 4 by making use of heat expansion and retraction of the delivery inner catheter and/or the stent device. The delivery inner catheter, the outer sheath 16 and the stent device 4 form a stent device delivery system.

What is claimed is:

1. A method comprising:
providing a delivery system comprising an outer sheath;
providing a stent device having a longitudinal lumen;
providing a mandrel having a plurality of coaxial cylindrical projections along a length of the mandrel;
securing the stent device onto the mandrel; and
pushing the mandrel into the outer sheath while maintaining contact between the plurality of coaxial cylindrical projections of the loading mandrel and an inner surface of the stent device thereby releasing the stent device into the outer sheath, wherein the plurality of coaxial cylindrical projections distributes axial forces along a full extent of the inner surface of the stent device as the loading mandrel moves the stent device longitudinally into the outer sheath.

2. The method of claim 1, wherein the inner surface is bare.

3. The method of claim 2, wherein the releasing step maintains high-friction between the mandrel and the stent device.

4. The method of claim 2, further comprising disposing an inner catheter within the stent device.

5. The method of claim 2, further comprising:
heating the stent device above a transition temperature; and
retracting the mandrel without disturbing the stent device.

6. The method of claim 5, further comprising disposing an inner catheter within the stent device.

7. The method of claim 2, wherein the stent device is a self-expandable stent device.

8. The method of claim 7, further comprising:
heating the stent device above a transition temperature; and
retracting the mandrel without disturbing the stent device.

9. The method of claim 8, further comprising shrinking the stent device onto the inner catheter by changing the stent device's temperature.

10. The method of claim 7, wherein the releasing step maintains high-friction between the mandrel and the stent device.

11. The method of claim 7, further comprising disposing an inner catheter within the stent device.

12. The method of claim 11, further comprising expanding the inner catheter within the stent device by heating the inner catheter.

13. The method of claim 11, further comprising shrinking the stent device onto the inner catheter by changing the stent device's temperature.

14. The method of claim 13, wherein the stent device further comprises a shape-memory alloy.

15. The method of claim 14, wherein the releasing step maintains high-friction between the mandrel and the stent device.

16. The method of claim 15, further comprising retracting the mandrel without disturbing the stent device.

17. The method of claim 16, further comprising heating the stent device above a transition temperature before retracting the mandrel.

18. The method of claim 1, wherein:
the stent device further comprises a bare inner surface; and
the releasing step maintains high-friction between the mandrel and the stent device.

19. The method of claim 18, further comprising disposing an inner catheter within the stent device.

* * * * *